United States Patent [19]

Reich et al.

[11] Patent Number: 5,288,489
[45] Date of Patent: Feb. 22, 1994

[54] FIBRINOLYSIS AND FIBRINOGENOLYSIS TREATMENT

[75] Inventors: Edward Reich, Setauket; Thomas G. Easton, Coram, both of N.Y.

[73] Assignee: Orion Therapeutic Systems, Inc., New York, N.Y.

[21] Appl. No.: 755,501

[22] Filed: Aug. 28, 1991

[51] Int. Cl.$^5$ ................ A61K 37/547; A61K 37/553
[52] U.S. Cl. .................................. 424/94.64; 424/529
[58] Field of Search .............. 424/94.64, 531, 557, 424/529, 530; 435/226, 174, 215; 530/381

[56] References Cited

U.S. PATENT DOCUMENTS

| | | | |
|---|---|---|---|
| Re. 32,271 | 10/1986 | Husain et al. | 435/215 |
| 3,950,513 | 4/1976 | Jensen | 424/94 |
| 4,051,011 | 9/1977 | Miyauchi et al. | 204/299 R |
| 4,083,961 | 4/1978 | Dussourdd'Hinterland et al. | 424/557 |
| 4,245,051 | 1/1981 | Reich et al. | 424/531 |
| 4,462,980 | 7/1984 | Diedrichsen et al. | 530/381 |
| 4,774,087 | 9/1988 | Wu et al. | 424/94.64 |
| 4,929,560 | 5/1990 | Edmunds et al. | 435/226 |

FOREIGN PATENT DOCUMENTS

| | | |
|---|---|---|
| 0182579 | 5/1986 | European Pat. Off. |
| 0253517B1 | 3/1992 | European Pat. Off. |
| 2497229 | 7/1982 | France |
| WO90/13323 | 11/1990 | PCT Int'l Appl. |

OTHER PUBLICATIONS

Knudsen, B. S., et al., "The Journal of Biological Chemistry," vol. 261(2), Aug. 15, 1986, pp. 10765–10771.
Silverstein, R. L., et al., "The Journal of Biological Chemistry," vol. 260(18), Aug. 25, 1985, pp. 10346–10352.
Loscalzo, J.; Chest, vol. 97(4), Apr. 1990–Supplement pp. 117S–123S.
International Search Report PCT US 92/06705.
K. Reddy and C. Wagner, Studies on the Stability of Plasmin, Chemical Abstracts, vol. 98, 1983, p. 330.
K. Takagi and Y. Yabushita, Antithrombotic Preparations for Medical Use, Chemical Abstracts, vol. 104, 1986, p. 393.
Ambrus et al., *The Pharmacologist*, 1:57 (1959).
Amris et al., *Danish Medical Bulletin*, 11:146–152 (1964).
Amris et al., *Scand. J. Clin. & Lab. Investigation*, 15:179–188 (1963).
Amris et al., *Scand. J. Clin. & Lab. Investigation*, 18:1–33 (1966).
Back et al., *Circulation Research*, IV:440–443 (1956).
Back et al., *J. Clin. Invest.*, 37:864–871 (1958).
Cliffton, *J. Am. Geriatrics Soc.*, 6:118–127 (1958).
Cliffton, *Annal. N.Y. Acad.Sci.*, 68:209–229 (1957).
Cook et al., *Trends in Pharmaceutical Sciences*, 11:444–451 (1990).
Dano et al., *Biochim. Biophys. Acta*, 566:138–151 (1979).
Duckert et al., in *New Concepts in Streptokinase Dosimetry*, Martin, Schoop & Hirsch, eds., Hans Huber Publishers, Bern-Stuttgart, 1978, pp. 175–178.
Edy et al., *Thrombosis Research*, 8:513–518 (1976).
Evans, C. H. in *Biochemistry of the Lanthanides*, Plenum Press, New York, pp. 85–125, 1990.
Hedner et al., *Blood*, 51:157–164 (1978).
Hirsh, in: *New Concepts in Streptokinase Dosimetry*, Martin, Schoop & Hirsch, eds. Hans Huber Publishers, Bern-Stuttgart, 1978, pp. 239–243.
Liu et al., *Canadian J. Biochem.*, 49:1055–1061 (1971).
Marbet et al., *Thromb. Haemostas.*, 48:187–189 (1982).
Marbet et al., *Thromb. Haemostas.*, 48:190–195 (1982).
Marbet et al., *Thromb. Haemostas.*, 48:196–200 (1982).
Matsuo et al., *Nature*, 291:590–591 (1981).
Mizutani et al., *Japanese Circulation J.*, 51:822 (1987).
Powell et al., *J. Biol. Chem.*, 255:5329–5335 (1980).
Shi et al., *J. Biol. Chem.*, 263:17071–17075 (1988).
Sottrop-Jensen et al., in *Progress in Chemical Fibrinolysis and Thrombolysis*, vol. 3, Davidson et al., eds. Raven Press, New York, 1978, pp. 191–209.
International Search Report, PCT/US92/06703.

Primary Examiner—Douglas W. Robinson
Assistant Examiner—Kristin Larson
Attorney, Agent, or Firm—Weingarten, Schurgin, Gagnebin & Hayes

[57] ABSTRACT

Disclosed is a fibrinolysis and fibrinogenolysis treatment which includes parenterally introducing into the body of a human patient human plasmin in fibrinolytically and fibrinogenolytically active form at a concentration and for a time sufficient to permit fibrinolytically and fibrinogenolytically active human plasmin to reach a concentration about the site of an intravascular clot sufficient to lyse the clot and/or to reduce circulating fibrinogen levels.

18 Claims, 4 Drawing Sheets

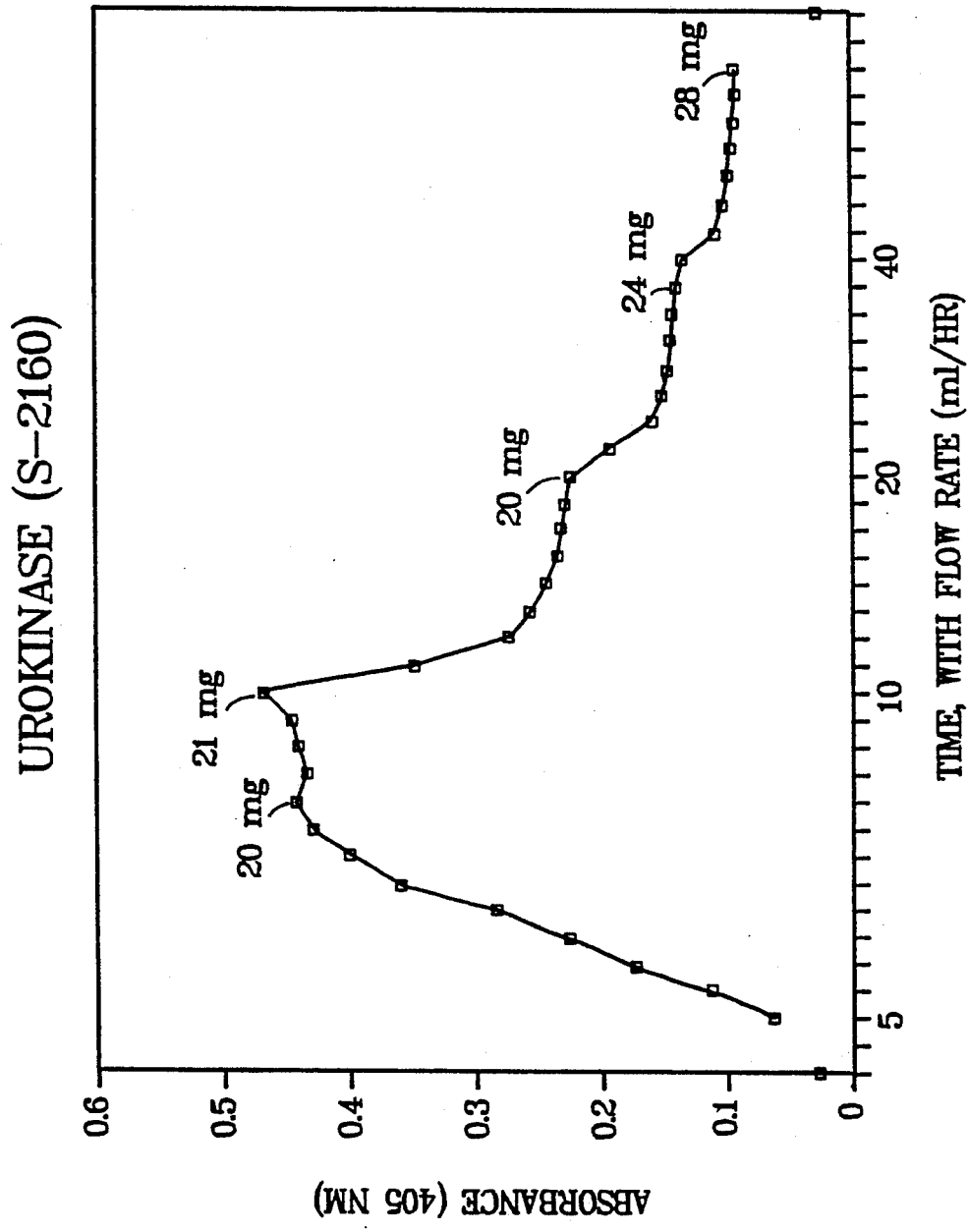

FIBRINOLYSIS AND FIBRINOGENOLYSIS TREATMENT

This invention relates to the treatment and prevention of thrombotic disorders.

BACKGROUND OF THE INVENTION

Thromboembolic disease, i.e., blockage of a blood vessel by a blood clot, affects many adults and can be a cause of death. Most spontaneously developing vascular obstructions are due to the formation of intravascular blood clots, also known as thrombi. Small fragments of a clot, emboli, may detach from the body of the clot and travel through the circulatory system to lodge in distant organs and initiate further clot formation. Heart attack, stroke, renal and pulmonary infarcts are well known consequences of thromboembolic phenomena.

A blood clot is a gelled network of protein molecules within which are trapped circulating blood cells, platelets, and plasma proteins. A major protein component of a clot is fibrin, which forms a relatively insoluble network in the clot. Proteolytic enzymes, particularly fibrinolytic enzymes, have been used to dissolve vascular obstructions, since disruption of the fibrin matrix results in dissolution of the clot. Clots are formed when soluble fibrinogen, which is present in high concentrations in blood, is converted to insoluble fibrin by the action of thrombin. Fibrinolytic enzymes dissolve the fibrin matrix of a clot, and fibrinogenolytic enzymes digest the fibrin precursor fibrinogen.

Intravascular clots may be removed after their appearance by means of enzymes capable of dissolving fibrin (fibrinolytic enzymes); and the probability of clot formation can be reduced by lowering the concentration of circulating fibrinogen, using enzymes that degrade fibrinogen (fibrinogenolytic enzymes).

Plasmin, a naturally-occurring fibrinolytic and fibrinogenolytic enzyme, is relatively unstable in the human circulatory system and, therefore, circulates primarily in its more stable inactive form, plasminogen. The activation of plasminogen to plasmin occurs by cleavage of a single arginyl-valine bond and is catalyzed by plasminogen activators. Urokinase and tissue plasminogen activator activate plasminogen by direct cleavage of the arginyl-valine bond. Streptokinase and staphylokinase are plasminogen activators of bacterial origin that activate plasminogen indirectly by forming a complex with plasminogen; this streptokinase-plasminogen complex behaves as a plasminogen activator that activates other plasminogen, molecules by cleaving the arginyl-valine bond.

Thromboembolytic therapies have involved the administration of a plasminogen activator; e.g., the direct intravenous injection of a plasminogen activator alone, the reinjection of a patient's plasma to which a plasminogen activator has been added ex vivo, the injection of plasma protein fractions previously mixed with streptokinase, or the injection of a preparation of porcine plasmin stabilized with added lysine in conjunction with streptokinase.

Fibrinogenolytic therapy aimed at reducing the risk of thrombosis has involved injection of snake venoms, e.g., *Angkistrodon rhodostoma*, which contain enzymes that degrade fibrinogen.

SUMMARY OF THE INVENTION

The invention features a fibrinolysis or fibrinogenolysis treatment which includes the parenteral introduction of human or mammalian plasmin or mini- or micro-plasmin into the body of a patient, the plasmin being in fibrinolytically/fibrinogenolytically active form, in an amount and for a time sufficient to permit the active plasmin to reach a concentration in the patient's bloodstream sufficient at least to reduce circulating fibrinogen levels.

In preferred embodiments, the amount of active plasmin and the duration of treatment permits the active plasmin to reach a concentration about the site of an intravascular clot sufficient to lyse the clot. In addition, or alternatively, the amount of active plasmin and the duration of treatment permits the active plasmin to reach a concentration sufficient to digest circulating fibrinogen at a rate sufficient to prevent the formation of a blood clot.

In preferred embodiments, fibrinolytically/fibrinogenolytically plasminogen or one or a mixture of its active analogs, is converted to fibrinolytically/fibrinogenolytically active plasmin, or the corresponding analog, extracorporeally, preferably by exposure to a physically contained, immobilized plasminogen activator, e.g., urokinase or tissue plasminogen activator or active analogs thereof, prior to the process of introducing the plasmin into the human body. Preferably, the plasminogen activator is covalently bonded to a matrix that may be, for example, a porous polymer membrane, e.g., nylon.

As used herein, "physically contained" plasminogen activator means the activator is insolublilized, entrapped, or encapsulated; "immobilized plasminogen activator" means that the plasminogen activator is matrix-bound, carrier-bound, or support-bound; a "physically contained" or "immobilized" plasminogen activator is prevented from accompanying the active plasmin into the body; "parenteral introduction" of a drug means the drug is introduced to the body other than by way of the gastrointestinal tract, e.g., intravenously, intraarterially, intraperitoneally, subcutaneously, intraocularly, or inhalationally; "extracorporeal" administration means from a point outside of the patient's body; and "substantially coincident" means either during the process of, i.e., at the same time as, or immediately prior to introducing the drug into the patient's body. The time period between the conversion of plasminogen to plasmin and injection of the plasmin into the body will typically be a period of 10 minutes, preferably 5 minutes, and most preferably less than 1 minute. The term "immediately prior to" means that the plasminogen to plasmin conversion and the introduction of plasmin into the patient occur close enough in time such that the active plasmin maintains at least 80%, preferably 90–99%, activity during that intervening time period. Preferably, human plasmin made according to the invention is substantially free of elements that interfere with its clot-lysing ability; i.e. it may be 98–99% pure plasmin, except for the presence of plasminogen in the plasmin sample.

As used herein, "clot lysis" refers to the partial or complete dissolution of a clot. As used herein, "mini-plasmin" or "mini-plasminogen" refers to that form of plasmin or plasminogen which contains, in addition to the enzymatic (i.e., catalytic) domain of the molecule, a single kringle; "micro-plasmin" or "micro-plasminogen" refers to a truncated form of plasmin or plasminogen which lacks all five kringles and the amino-terminal domain (i.e, preceding the first kringle); "mammalian" plasmin refers to both human and non-human plasmins, the non-human forms include but are not limited to bovine, porcine, or ovine plasmins.

In other preferred embodiments, fibrinolytically/fibrinogenolytically inactivated plasmin (inhibited plasmin), or an inactive analog thereof, is converted to active plasmin or its analog extracorporeally, by exposure to a substance capable of removing an inhibitor and/or stabilizer of the active plasmin, wherein the removal results in plasmin reactivation. The inhibitor preferably includes lauryl sulfate or similar hydrophobic anions or cations, which reversibly inhibit the enzymatic activity of plasmin. The inhibitor removing substance may include an adsorptive matrix or an ion exchange resin.

Analogs of plasminogen or plasmin include but are not limited to glu-, lys-, or mini- or micro-plasmin or any amino acid sequence having at least 70% homology with plasminogen or plasmin or their truncated forms and possessing the enzymatic properties of either molecule. Plasminogen may be purified natural plasminogen, or may be chemically synthesized or expressed from recombinant DNA. Generally, the invention is unlimited with respect to the type of plasmin active substance employed, be it natural form, truncated, or an analog of plasmin, and for the purpose of the invention, all such forms are considered in material respects to be embraced within the term "plasmin". Analogs of urokinase or tissue plasminogen activator include those proteins having amino acid insertions, substitutions, or deletions which result in a molecule having plasminogen activating activity; such analogs would include truncated forms of these molecules.

Another aspect of the invention features a stabilized enzymatically inactive plasmin composition including hydrophobic ions comprising branched or straight chained alkyl groups having from about eight to about 20 carbon atoms linked to an anion group, preferably a sulfur containing anionic group such as sulfate, a cationic group such as quaternary ammonium, or both. The currently preferred hydrophobic ions are lauryl sulfate ions. These compositions are characterized by the ability to be reactivated upon removal of the ions by, for example, an appropriate ion exchange medium.

Fibrinolysis or fibrinogenolysis treatment according to the invention is useful to treat or prevent heart attack, stroke, and thromboembolic vascular occlusion, with or without associated organ infarction. The risk of developing a thrombus can also be reduced according to the invention, e.g., for diabetics, who have an increased risk of developing thrombi, or for pregnant women or women who use oral contraceptives, who have an increased risk of thrombophlebitis. The amount of plasminogen activator required for fibrinolysis treatment according to the invention is a small fraction of that required for plasminogen activator injection therapy to dissolve blood clots, and that small fraction may be used a number of times. In addition, since the plasminogen activator remains extracorporeal during treatment, it will escape the rapid physiological turnover to which plasminogen activators are normally subjected in the circulatory system; likewise, it will also avoid contact with the patient's immune system, and thus the patient will not mount an immune response to it. Consequently, plasminogen activators used in accordance with the invention may be derived from human as well as non-human sources.

Administration of active human plasmin according to the invention is, therefore, simple, economical, adaptable to individual patient needs, and does not require the use of foreign proteins or drugs which may in themselves have unwanted side-effects, e.g., an immune reaction. Administration of mammalian mini- or micro-plasmin will also have these advantages and, due to the truncated form of these molecules, potentially will not raise a significant immune response when administered to a patient. The administration of non-human mammalian truncated plasmins can be performed according to the invention because these truncated versions of plasmin contain little more than one-third (i.e., the active region) of the plasmin molecule, and therefore presumably present fewer foreign epitopes for the human immune system to respond to.

The treatment of thromboembolism according to the present invention is suitable for acute episodes requiring short-term treatment or for more long-term, continuous or intermittent courses of treatment. Pharmacological variables associated with introduction of drugs into the body, e.g., the rate of inhibition or inactivation of or the removal of plasminogen activators from circulation, do not play a role in thrombolytic therapy according to the invention since the plasminogen activator remains extracorporeal. In addition, individual patient needs can be accommodated by administering a precise amount of plasmin to the patient that has been adjusted to individual factors, e.g., the amount of circulating inhibitors of plasmin.

The course of therapy can be monitored, if desired, e.g., by repeated estimation of the patient's circulating inhibitor levels, during treatment periods of any duration, thereby permitting the dynamic adjustment of therapy. In therapies based on injected plasminogen activators a large fraction of the patient's plasminogen is consumed, thereby limiting the extent, duration and frequency of therapy. In therapy according to the invention there is no depletion of patient's plasminogen, which remains available; and the extracorporeal reservoirs of both plasminogen and activators are unlimited, permitting treatments of unrestricted frequency and duration.

BRIEF DESCRIPTION OF THE DRAWINGS

FIG. 1B is a graph showing hydrolysis of KABI S-2160 substrate in the presence of membrane-bound enzyme.

DESCRIPTION

Figure 1A:
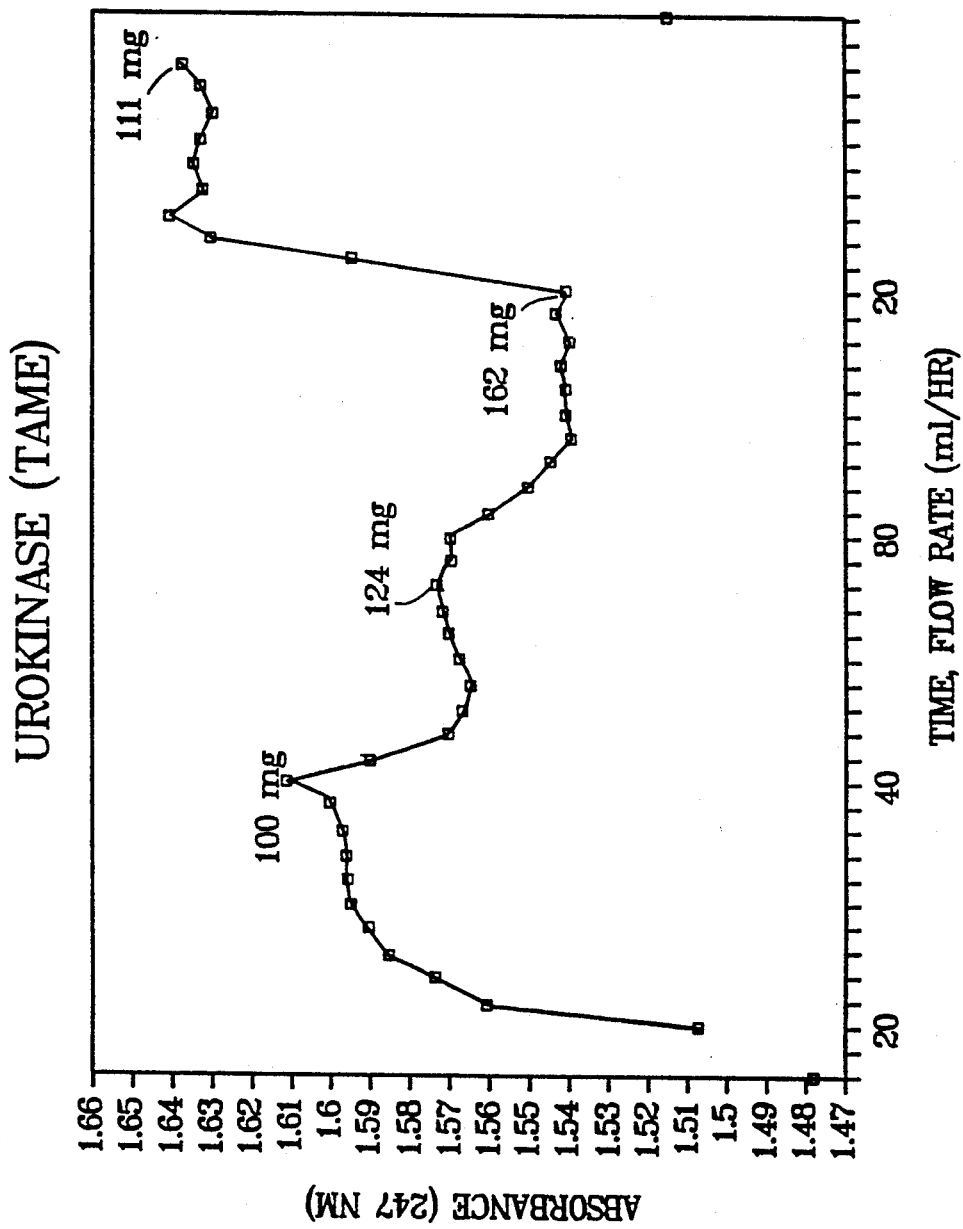
FIG. 1A is a graph showing hydrolysis of TAME substrate in the presence of membrane-bound enzyme.

A patient suffering from vascular obstruction, e.g., a victim of heart attack, stroke, or renal or pulmonary infarction, or at high risk of developing vascular obstruction or peripheral vascular disease, may be treated according to the invention by administration of extracorporeally-activated or reactivated plasmin to the patient. The extracorporeal activation of plasminogen is achieved by immobilizing a plasminogen activator on a matrix having a large surface area, e.g., a porous membrane, and perfusing the membrane with a solution of human plasminogen in its native or truncated forms. The membrane is mounted in a device close to the site of injection. Plasminogen is activated upon encountering the immobilized plasminogen activator while traversing the membrane, and the plasmin formed passes immediately into the bloodstream.

The invention is based primarily on the realization that fibrinolytic and fibrinogenolytic therapy can be conducted effectively and can be controlled by direct infusion of active forms of plasmin despite plasmin's notorious instability and propensity for autodigestion. Broadly, this is accomplished by treating a stabilized plasmin preparation to remove stabilizing moieties, or catalytically or otherwise producing active plasmin from a plasmin precursor such as plasminogen, just prior to parenteral infusion. The means by which the infusable, active plasmin is produced at the treatment site does not per se comprise an aspect of this invention, except as set forth in the claims. Currently preferred devices for implementing the invention are disclosed herein to enable those skilled in the art to make and use the processes of this invention. For further particulars of apparatus suitable for use in this invention, see copending application Ser. No. 07/750920, filed on the same day as this application, the disclosure of which is incorporated herein by reference.

As noted above, purified plasmin is chemically unstable due to its susceptibility to proteases, and its tendency to self-digest. Included in the invention is the discovery that certain hydrophobic ions inhibit the autolytic activity of plasmin. Lauryl sulfate ions are inhibitors of plasmin when present in amounts, depending on protein concentration, equal to or greater than 0.05%. Other hydrophobic anions or cations which may have the same effect and are readily separable are sarcosyl, deoxycholate, and cetyltrimethyl ammonium halides. Generally, useful hydrophobic ions comprise moieties having 8 to 20 carbon atoms attached to one or more ionic groups such as sulfate, sulfonate, phosphate, or quaternary ammonium. The invention thus also includes the extracorporeal reactivation of inactive plasmin; e.g., a mixture of plasmin and a reversible inhibitor of plasmin, e.g., lauryl sulfate, which may be reactivated extracorporeally by removal of the inhibitor just prior to injection of the plasmin using, for example, an ion exchange resin.

Fibrinolysis and fibrinogenolysis treatment according to the invention is described below, including preparation of immobilized plasminogen activator and substrate plasminogen or substrate derivatives, preparation of a stable mixture of inactive plasmin, the reactivation of inactive plasmin, and fibrinolysis treatment in vivo by direct injection of purified active plasmin.

Preparation of Immobilized Plasminogen Activator

Immobilized plasminogen activator may be prepared using a support consisting of nylon membrane, of $1-3\mu$ average pore size, (Pall Corporation, Glen Cove, N.Y.). In its preferred version, such a membrane bears a high density of unsubstituted carboxylate groups (Pall. No.BNPCH5 or BNNCH5), which act as starting points for chemical modifications that allow anchoring of proteins.

Nylon membrane sheets are cut into the shape of discs of desired diameter and derivatized as follows. A solution of 0.5M spermine tetrahydrocholoride in water is brought to pH 7.0-7.1 by the careful addition of NaOH; separately, a solution of a water soluble carbodiimide, preferably 1-ethyl-3-(3-dimethylaminopropyl) carbodiimide hydrochloride (EDAC), (0.5M in water) is brought to pH 5.0-5.05 by the addition of dilute hydrochloric acid; the two solutions are mixed in equal amounts and membrane discs are immersed in the mixture and incubated overnight at room temperature. The discs are washed copiously first with distilled water and then with 1.0M $NaHCO_3$. The discs are then packed in solid, finely-pulverized succinic anhydride (500 mg per $cm^2$ disc surface area), and sufficient dipotassium hydrogen phosphate (0.5M) is added to thoroughly irrigate the disc and succinic anhydride packing (ca. 0.3-0.5 $ml/cm^2$ disc area). The reaction is allowed to proceed overnight at room temperature. Small sample discs are incorporated alongside the membranes being treated and tested for the presence of residual free amino groups. This succinylation procedure can be repeated, if necessary. The succinylated discs are rinsed free of precipitated succinate, washed under suction first with $NaHCO_3$ (0.5-1.0M) and then with water, and dried. The discs may be stored for months at room temperature, with no change in properties.

The dried membrane filter discs are mounted and securely clamped in holders that permit them to be perfused, and the entire assembly is incorporated into a circuit, driven by a peristaltic pump, in which the discs are continuously perfused for at least 1 hour at >30° C. with a solution of N-hydroxysuccinimide and EDAC, both at 50 mM, in pure tertbutanol. At the end of the perfusion, the mounted discs are perfused briefly with 1 mM HCl at room temperature, blotted, swirled in ice-cold distilled water for a few minutes, then placed in a shallow dish, previously rinsed with 0.5% detergent Triton X-100 in water, whose diameter is just sufficient to accommodate the membrane discs. The carboxylate groups have now been activated for protein coupling.

Highly purified human urinary urokinase is coupled to the membrane discs immediately after activation as follows. Lyophilized urokinase, e.g., WINKINASE (Winthrop Laboratories, Division of Sterling Drug, Inc., New York, N.Y.), or UKIDAN (Serono, Aubonne, Switzerland) is dissolved in 10 mM HEPES, pH 7.0-7.4 at a concentration of 4-5 mg per ml. Sufficient solution is pipetted into small shallow dishes so as to thoroughly impregnate the activated membranes, e.g., 15-20 $\mu l/1$ $cm^2$ of membrane. A total of approximately 400 $\mu g$ or 1.2 mg urokinase is used to impregnate a membrane of 25 mm or 47 mm diameter, respectively. After immersing the membranes in urokinase solution, the dishes are sealed, and incubated in a moist chamber at 4° C. for 14-16 hours, preferably with gentle rocking agitation. The coupled membrane is rinsed with 1 mM HCl by low speed centrifugation in a polypropylene tube, and the rinsing fluid collected, pooled with residual incubation medium, and assayed for remaining non-membrane-bound urokinase.

Assay of Membrane Bound Urokinase

Membrane bound enzyme is assayed by pumping substrate, either small and synthetic, or macromolecular protein substrates (plasminogens), through the membrane; the former measures the amount of active enzyme bound, whereas the latter yields an estimate of the catalytic capacity of the membrane in plasminogen activation. The membrane to be assayed is mounted in a filter holder (for example, Millipore Nos. SX0002500 and SX0004700 for 25 mm and 47 mm diameter, respectively), which is connected to a peristaltic pump. Temperature control may be achieved by immersing the substrate reservoir and connecting tubing in a temperature regulated bath. The substrate solution is pumped through the membrane, or several membranes assembled in series, e.g., 1 ml aliquots of the effluent are taken. The absorbance change in the effluent compared with the substrate solution gives the concentration of product which, multiplied by the flow rate, yields the activity in terms of moles per unit time for small substrates; assay of plasmin using KABI S-2251 is used for estimating the rate of plasminogen activation. Given the value of apparent $K_{cat}$, which is derived from measurements of enzyme activity in free solution, the estimate of active bound enzyme is easily obtained from the observed rate of product formation. In practice, assay of bound enzyme activity should be made under conditions of perfusion in which no more than 10% of small substrates are hydrolysed; flow rates of 10-15 ml/cm$^2$/h give maximum apparent rates of substrate hydrolysis.

The small substrates dissolved in Tris-HCl buffer (0.1M, pH 8.8) are either TAME (tosyl-L-arginine methylester, 10 mM) or KABI S-2160 (N-benzoyl-phe-val-arg-p-nitroanilide, 0.2 mM). The hydrolysis of TAME is measured by change in absorbance at 247 nm, and that of KABI S-2160 at 405 nm. An illustration of the results of such an assay is given in FIG. 1.

Preparation of Substrate Plasminogen

Human plasminogen is prepared at 4° C. according to a modified procedure of Liu et al., *Canadian J. Biochem.* 49:1059-1061 (1971). Five hundred grams of frozen Cohn fraction III or II & III paste is pulverized at 4° C. using a mortar and pestle, then added in portions with constant stirring to 5 liters of phosphate buffered saline (PBS), containing 1 μM p-nitrophenyl-p-guanidinobenzoate. Stirring is continued for 4-5 hours, until the paste is fully and evenly suspended. The solution is then centrifuged at 12000 ×g for 20 minutes at 4° C., gelatinous pellet discarded. The supernatant is filtered under gravity through "fast" filter paper, then brought to 10% of saturation (e.g. 50 g/l), by the addition of solid ammonium sulfate, and centrifuged once again at 12000×g for 20 minutes at 4° C. The resulting pellet is discarded, and the lipid-like material floating on the supernatant removed by filtration through a gauze plug.

The filtered supernatant is then pumped, e.g., at 600-900 ml per hour, into e.g., a 230 ml, 4.8×15 cm column packed with G-15 SEPHADEX in PBS, and the outflow passed directly into a second column, of, e.g., 750-800 ml volume and 10 cm. in diameter, packed with lysine-agarose (Pharmacia 4B or 6B) and pre-equilibrated with PBS. The entire system is washed with PBS (e.g., 250 ml), the G-15 column disconnected, and the lysine-agarose column is washed with an additional 1.5 column volumes of PBS until the $A_{280}$ drops below 0.15. The column is then washed with 1 column volume of a solution consisting of 4 parts of ethylene glycol and 6 parts of potassium phosphate buffer (0.5M, pH 8.0), followed by one column volume of PBS. Plasminogen is then eluted from the column with a linear gradient (2.5-3 column volumes) of epsilon aminocaproic acid (0-25 mM) PBS, and collected in fractions. The fractions having the highest concentration of protein are pooled and precipitated at 50% saturated ammonium sulfate in the presence of benzamidine (50 mM), the pH being kept near neutrality by periodic addition of small volumes of tris-hydroxymethyl aminomethane (tris) base (1M).

The precipitated plasminogen can be stored under 50% saturated ammonium sulfate containing 50 mM benzamidine for many months with no loss of activity. After desalting and redissolving in PBS, it can be used directly for generating plasmin as described below.

Preparation of Substrate Mini-plasminogen

Mini-plasminogen is prepared according to a modified procedure of Powell et al., *J. Biol. Chem.* 225:5329-5335 (1980). The plasminogen precipitate, e.g., 300 mg, is suspended in ammonium sulfate-benzamidine, as described above, centrifuged at 10,000×g for 30 minutes at 4° C. and the resulting supernatant discarded. The pellet is dissolved in a minimum volume e.g., 15-20 ml, of 100 mM NaCl—50 mM Tris, pH 8.0, at 4° C. and desalted by passage through a 230 ml, 4.8×15 cm column of G15 SEPHADEX in the cold. Protein-containing fractions eluted from the column are pooled and diluted at room temperature with starting NaClTris buffer to 3 mg/ml. 20,000 Kallikrein inhibitor units of aprotinin, and 1.7 mg pancreatic elastase are then added to the pooled protein fractions and the solution is incubated at room temperature with gentle stirring for 5 hours. The reaction is terminated by addition of methoxysuccinyl-(-ala-ala-pro-val) chloromethylketone to 10$^{-4}$M, and stirred for a further 30 minutes. The solution is dialyzed overnight at 4° C. against a large volume of 0.1M sodium phosphate buffer, pH 8.0, using tubing with molecular weight cutoff at 6500. 300 mg of dialyzed plasminogen in solution is applied to a 4.8×15 cm, 230 ml lysine-agarose column equilibrated in 0.3M sodium phosphate buffer, pH 8.0, and mini-plasminogen is eluted in 300 ml of the same buffer. Protein-containing fractions are pooled, benzamidine added to a final concentration of 50 mM, and miniplasminogen precipitated by the addition of solid ammonium sulphate in several portions to a final concentration of 80% saturation.

The macromolecular substrates glu- and lys-plasminogen as well as truncated forms such as mini- and/or micro-plasminogen are dissolved usually at a concentration of about 30 μm in 90 mM NaCl, 5 mM NaPO$_4$, pH 7.3-7.5, 1.8% dextrose, Glu-plasminogen is the naturally occurring form of plasminogen in circulation; the N-terminal amino acid residue is glutamic acid. Lys-plasminogen, having an N-terminal lysine residue, is derived from glu-plasminogen by limited proteolysis, usually catalyzed by plasmin, whereby a peptide fragement 77 residues long is cleaved from the amino terminal domain. Mini-plasminogen is derived from either glu- or lys-plasminogen by limited proteolysis, catalyzed by pancreatic elastase, whereby a fragment consisting of the proenzyme domain of plasminogen with a single attached kringle is generated, the remaining 4 kringles and intervening peptides having been separated. (Sottrup-Jensen, L. et al., *Prog. in Chemical Fibroinolysis and Thrombosis* 3:191-209 (1978) Davison, J. et al., Eds., Raven Press, NY). Microplasminogen consists of the proenzyme domain of plasminogen with a stretch of connecting peptide and a few residues of kringle 5 attached at its N-terminal end; it is generated by the action of plasmin on plasminogen (Shi, G. -Y., and Wu, H. -L., *J. Biol. Chem.*, 63:17071-5 (1980).

The rate of plasminogen activation, as well as the fraction that is activated to plasmin are influenced by numerous factors, including plasminogen concentration, flow rate, membrane area, enzyme binding area within the reaction zone, and numbers of membranes in series within the reaction zone. These parameters can be adjusted to achieve any desired therapeutic goal in terms of plasmin formed per unit time for any fraction of plasminogen activated. In a typical run, two 47 mm membranes mounted in series will activate approximately 80% of the perfused mini-plasminogen at a concentration of 30 μM and a flow rate of 70 ml/hour, yielding about 1.7 μmoles of mini-plasmin/hour. Membranes can function continuously at constant rates for at least 3 hours.

When membrane coupling is performed, 80% of available urokinase is removed from solution and bound to the membrane. Of this amount, 20-25% is catalytically active in hydrolysis of small substrates, and approximately 5% is active in plasminogen activation.

Figure 2:
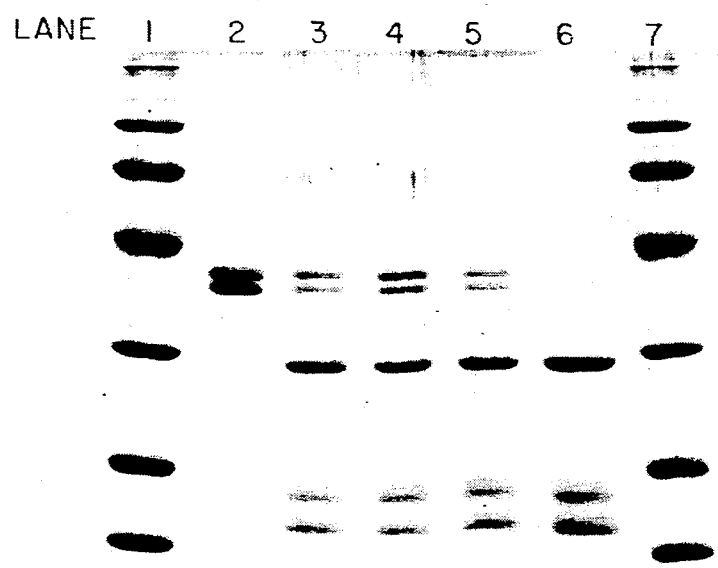
FIG. 2 is an SDS polyacrylamide gel of mini-plasminogen activated by membrane-bound urokinase.

In FIG. 2, samples were run on an SDS-polyacrylamide gel with 2-mercaptoethanol (12½% acrylamide). Lane two contains mini-plasminogen, whose molecular weight is somewhat less than that of ovalbumin. In this preparation, mini-plasminogen appears as two closely spaced bands. Lanes three to six contain sequential samples after perfusion of mini-plasminogen through porous nylon membranes containing immobilized urokinase. The perfusion rate for samples in lanes three to five was about 70 ml/hr. The major band from mini-plasmin is the light (or B) chain, at a molecular weight just below that of carbonic anhydrase; the amino terminal fragments of mini-plasmin appear as a doublet between soybean trypsin inhibitor and lysozyme. For the sample in lane six, the perfusion rate was reduced to about 35 ml/hr; the proportion of unactivated mini-plasminogen is decreased relative to lanes three to five, and the proportion of plasmin light chain is increased. Lanes one and seven contain molecular weight reference standards. These are (from top to bottom): phosphorylase b 97,400 daltons; bovine serum albumin 66,200 daltons; ovalbumin 45,000 daltons; carbonic anhydrase 31,000 daltons; soybean trypsin inhibitor 21,500 daltons; and lysozyme 14,400 daltons.

Preparation of Stored Inactive Plasmin

A second fibrinolytic treatment according to the invention also involves the direct infusion of highly purified plasmin. This plasmin is prepared, stored, and formulated in advance. Plasmin exhibits, like any proteases, a strong tendency to self-digestion, especially under the conditions of high concentration that are encountered during its preparation, storage and formulation for delivery. It is desirable to prevent autolysis in order to preserve catalytic activity. A preferred way of accomplishing such suppression is by the addition of suitable concentrations of lauryl sulfate ions, in the form of sodium lauryl sulfate, which inhibits plasmin-catalyzed proteolysis. However, lauryl sulfate can be toxic and, therefore, must be completely removed from the plasmin preparation prior to injection. This is conveniently accomplished by passing the solution of plasmin and lauryl sulfate over a matrix capable of removing lauryl sulfate either by adsoption and/or ion exchange. Thus, the plasmin is activated coincident with its injection into the patient's body.

All operations are performed under sterile conditions using sterile, pyrogen-free reagents. Plasmin, or one of its truncated forms (mini- or micro-plasmin) is produced by perfusing the corresponding plasminogen through one or more urokinase membranes, prepared as described above. The flow rate, plasminogen concentration, temperature and numbers of membranes in series are selected to activate at least 95% of the perfused plasminogen to plasmin; for example, two 47 mm membranes perfused with 30 μM miniplasminogen at approximately 50 ml/hr and 25° C. The effluent is collected directly into a chilled vessel containing a solution of sodium lauryl sulfate sufficient to yield a final sodium lauryl sulfate concentration of 0.05-1.0%, e.g., a solution of 0.5-10% sodium lauryl sulfate in a volume of buffered $H_2O$ one tenth that of the anticipated final volume of effluent to be produced. Alternatively, to achieve a greater proportion of plasmin in the final product, the effluent may be led through a refrigeration bath and directly onto a column bed of immobilized plasmin inhibitor (e.g. aprotinin), where it is bound in an inhibited state; the material emerging from this bed contains the remaining, unactivated plasminogen which may be recycled onto the urokinase membrane to achieve a substantially complete conversion to plasmin.

At the termination of plasminogen activation, any residual unactivated plasminogen is removed by washing the column bed with PBS buffer, and the plasmin product is recovered by elution with 90 mM NaCl-1 mM HCl, and collected into a buffered solution of sodium lauryl sulfate, designed to neutralize the HCl, as indicated above. The inactive plasmin is concentrated by the addition of solid ammonium sulfate to 80% of saturation, the precipitated plasmin is collected by centrifugation, the ammonium sulfate removed by dialysis against large volumes of water containing sodium lauryl sulfate (0.1%) and 90 mM NaCl, and the dialyzed plasmin solution lyophilized. For therapeutic administration, the inactive plasmin is reconstituted by addition of sterile, pyrogen-free water containing 1.8% of dextrose, 90 mM NaCl and 0.1% lauryl sulfate, final concentrations. The inactive plasmin solution is then perfused through a matrix capable of retaining lauryl sulfate ions and thus removing them from the plasmin preparation. For example, the inactive plasmin solution may be pumped through column of EXTRACTIGEL (Pierce Chemical Co., Rockford, Ill.), an adsorbing matrix, at a rate not exceeding 1 ml per $cm^2$ per minute. The lauryl sulfate ions are thus retained by the matrix and reactivated plasmin is produced.

Alternatively, the lauryl sulfate-stabilized plasmin may be activated by contacting it with a plurality of ion exchange resin particles. The particles may vary in size, e.g., from 10-350 mesh, and the resin may be any conventional material capable of adsorbing lauryl sulfate ions, e.g., AG11 A8 (Bio-Rad Laboratories, Richmond, Calif.).

Experimental Fibrinolysis

The fibrinolysis treatment of the invention, in which human plasmin is directly administered to a patient, can be tested in vivo by introducing a radioactive clot into, e.g., the external jugular vein of a dog, and injecting plasmin using the apparatus of the invention into the dog's circulatory system. Dissolution of the clot may be followed by monitoring the level of radioactivity; a decrease in the level of radioactivity at the site of the clot indicates dissolution of the clot.

Testing is performed using a plasmin preparation of the invention. A clot is prepared using freshly-drawn, anticoagulated and then recalcified whole human blood to which a small amount of $^{125}$I-labeled, highly purified human fibrinogen has been added. The clot is secured in a stainless steel coil that is introduced into and lodged in the external jugular vein; the use of radioactive clots prepared ex vivo has previously been described by Matsuo et al., (*Nature* 291:590 (1981)). The clot is introduced into healthy, well-conditioned male hounds, at least 20 kg in weight, which have been fasted overnight and prepared for surgery under standard conditions. One side of the neck, and the ipsilateral fore and hind legs are shaved, catheters are placed in the respective cephalic and saphenous veins, and the animals anesthetized by the intravenous administration of thiamylal sodium (20 mg/kg). An intratracheal tube is then inserted, and the animals maintained on inhalational anesthesia consisting of nitrous oxide:oxygen 2:1 containing 1-2% halothane. Physiological saline is dripped through both catheters at a slow maintenance rate (2-3 drops per minute). The skin overlying the external jugular vein is incised (2-3 inches) parallel to the vein, and the internal and external maxillary veins exposed by blunt dissection for about 2 inches before their confluence; a similar exposure is practiced for the external jugular vein. The internal maxillary vein is ligated, anteriorly, leaving an accessible length of about 2 inches before the confluence, the external maxillary and external jugular veins are clamped, and the clot is set in place. The clamps are removed to reestablish blood flow, a gamma detector is placed directly above, <5 mm from the surface of the vein, and the radioactivity monitored at 10-20 minute intervals. Two urokinase-membrane filters in series are connected to the catheter in the cephalic vein and mini-plasminogen (30 $\mu$M) dissolved in 90 mL NaCl, 10 mM Na phosphate pH 7.3-7.4, 1.8% dextrose, is pumped through at a rate of 70 ml/hr.

Figure 3:
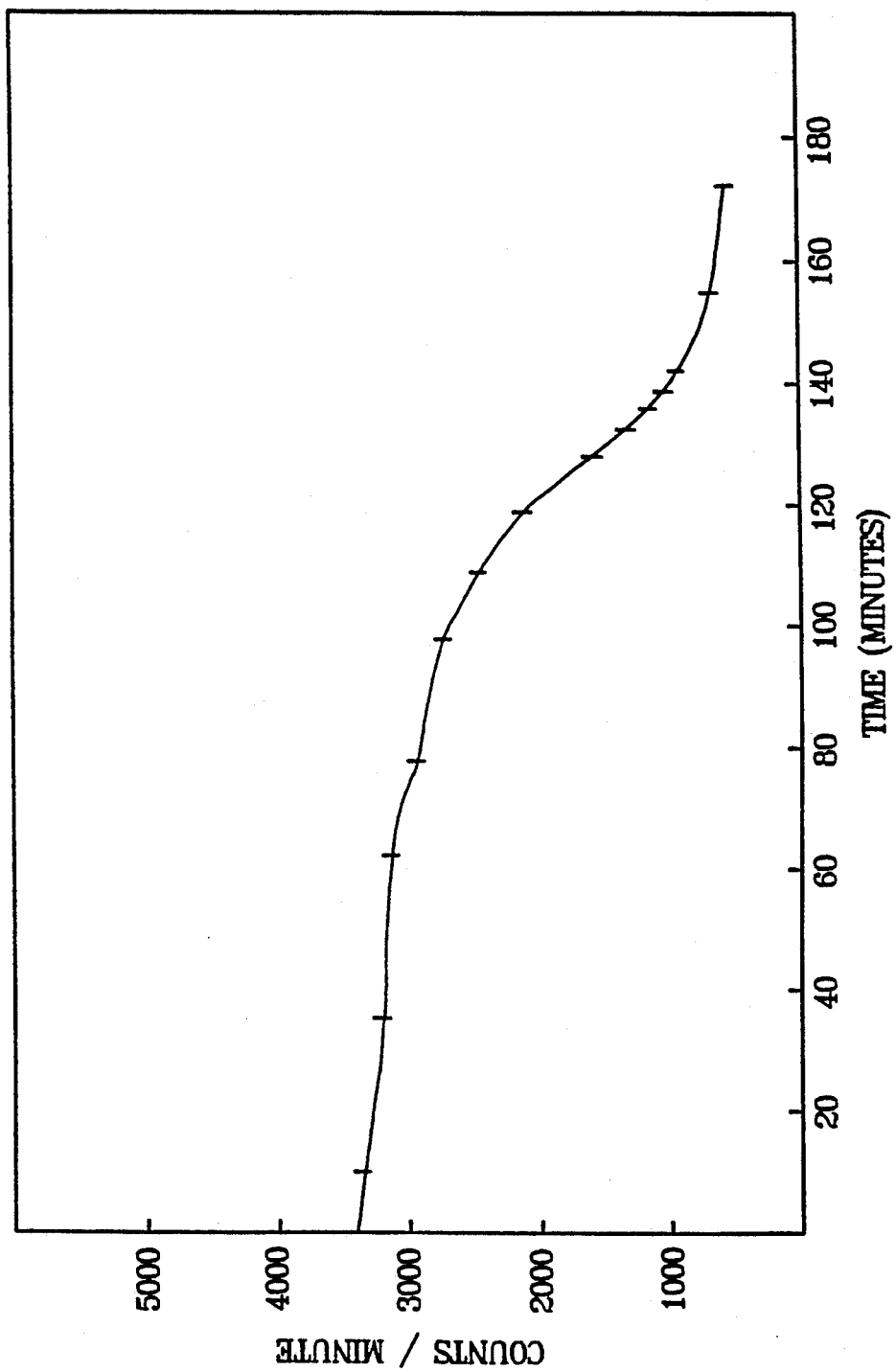
FIG. 3 is a graph of radioactivity levels recorded from a monitor overlying a radioactive blood clot in a dog.

The radioactivity level registered by the detector is recorded as a function of time after onset of the mini-plasmin infusion. A decrease in radioactivity at the site of the clot indicates dissolution of the fibrin clot. Six separate experiments using dogs fitted with intravenous clots were performed, and the results demonstrated essentially complete clot lysis in reproducible time periods in each experiment. FIG. 3 is a graph of results in which radioactivity levels were recorded from a monitor overlying a radioactive blood clot inserted in the external jugular vein of a dog. Radioactivity is recorded as a function of time following the onset of infusion of mini-plasmin which was generated by perfusing mini-plasminogen through a nylon membrane containing immobilized human urokinase.

Blood samples are aspirated from the saphenous vein at timed intervals, and are assessed for fibrinogen content by determining clottability, either spontaneous or following addition of human thrombin (0.25 unit per ml, final concentration), aprotinin having been added to block any plasmin activity. These determinations reveal that fibrinogen decreases progressively from the onset of the infusion, its removal being essentially complete in about one hour under these conditions.

Other fibrinolytic treatments, which involve a chosen plasminogen activator and a given preparation of plasminogen may also be tested in the a system described above. Parameters such as concentration of active plasmin administered, duration of treatment, type of plasminogen activator, and type of membrane, etc., may be varied, and these variations may also be tested in such a canine system.

Dosage and Use

Methods of the invention include fibrinolytic/fibrinogenolytic treatments, the dissolution of intravascular thrombi, and reduction of the risk of thrombus formation. Persons at risk for thrombus formation include but are not limited to diabetics and pregnant women. Diabetics carry a higher than normal level of fibrinogen and, therefore, have a higher risk of developing thrombi. The administration of plasmin prophylactically to a diabetic would lower fibrinogen levels and thus reduce the risk of clot formation.

The duration of fibrinolytic and/or fibrinogenolytic treatment according to the invention may vary from a short single dose administration of plasmin, e.g., 1-30 $\mu$moles of plasmin for a 150 lb. person within a 6 hour period to much larger quantities during continuous or intermittent administration for days to weeks, depending upon the size and location of the clot. For example, if the clot is venous, the duration of treatment may be days, whereas if the clot is arterial, only hours of treatment may be required. Short, single dose treatments may be required for conditions such as myocardial infarction; longer thrombolytic regimens for thrombophlebitis and pulmonary embolism; and prolonged, continuous and/or intermittent treatment may be used to treat coronary occlusion and other conditions for which prophylactic therapy may be desirable, e.g., to reduce the risk of clot formation. Continuous treatment includes the uninterrupted administration of plasmin; intermittent therapy includes the administration of plasmin which is interrupted by minutes, days, or weeks. A longer thrombolytic or fibrinolytic/fibrinogenolytic therapy will require adjustment depending upon the ultimate desired level of circulating fibrinogen. If a small reduction in fibrinogen concentration is required, more frequent injections of low doses may be needed to maintain a given depression of the fibrinogen level.

Clot dissolution reflects the fibrinolytic action of plasmin, and the duration and effectiveness of thrombolytic therapy following administration of plasmin depend primarily on the balance between the rates of plasmin introduction, and plasmin removal and/or inhibition by the plasmin inhibitor, $\alpha$2-antiplasmin, or other inhibitors of plasmin. Factors to be taken into account when adjusting plasmin dosage for clot dissolution include physical factors such as height, weight, and age of the patient; the location of the blood clot, and circulating levels of plasmin inhibitors, such as $\alpha$2-antiplasmin and $\alpha$2-macroglobulin. $\alpha$2-antiplasmin, which has a normal range of plasma concentration in vivo of approximately 1 $\mu$M$\pm$20%, is ordinarily the dominant factor regulating plasmin action in the circulation; plasmin combines irreversibly with $\alpha$2-antiplasmin to form a 1:1 complex and is thereby inhibited before it can attack clots or other proteins. The level of circulating $\alpha$2-antiplasmin is important in assessing plasmin dosage, and $\alpha$2-antiplasmin must be titrated to a level at which no more than 15% of the normal circulating concentration is present. A high initial level of $\alpha$2-antiplasmin will require a large dose of extracorporeal plasmin to be administered parenterally.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. A fibrinolysis and fibrinogenolysis treatment comprising the step of:

parenterally introducing into the body of a human patient in need thereof a therapeutically effective amount of human plasmin or mammalian mini- or micro-plasmin in fibrinolytically/fibrinogenolytically active form in an amount and for a time sufficient to permit said active plasmin to reach a concentration in the bloodstream of said patient sufficient to reduce the level of circulating fibrinogen, wherein, substantially coincident with parenteral introduction of said active plasmin into said patient, fibrinolytically/fibrinogenolytically plasminogen, or an analog thereof, or stabilized inhibited plasmin, is converted to said fibrinolytically/fibrinogenolytically active plasmin ex vivo.

2. The process of claim 1 wherein the amount of plasmin introduced into the patient and time during which the plasmin is introduced are sufficient to permit said active plasmin to reach a concentration at the site of an intravascular clot sufficient to lyse said clot.

3. The process of claim 1 wherein said amount and time are sufficient to permit said active plasmin to reach a concentration sufficient to digest circulating fibrinogen at a rate sufficient to prevent the formation of a blood clot.

4. The process of claim 1 wherein said conversion is accomplished upon exposure of said fibrinolytically/fibrinogenolytically plasminogen to an extracorporeal plasminogen activator.

5. The process of claim 4 wherein said conversion is accomplished upon exposure of said plasminogen to a physically contained plasminogen activator.

6. The process of claim 5 wherein said physically contained plasminogen activator is immobilized.

7. The process of claim 5 wherein said conversion is accomplished upon exposure of said plasminogen to a plasminogen activator that is covalently bonded to a matrix.

8. The process of claim 7 wherein said conversion is accomplished by exposure to a plasminogen activator covalently bonded to a matrix comprising a porous polymer membrane.

9. The process of claim 8 wherein said conversion is accomplished by exposure to a plasminogen activator covalently bonded to a matrix of nylon.

10. The process of claim 1 wherein said plasminogen is selected from the group consisting of glu-, lys-, mini- or micro-plasminogen, and an analog thereof, substantially free of elements that interfere with clot-lysing or fibrinogenolytic ability.

11. The process of claim 1 wherein said plasminogen is selected from the group consisting of purified natural plasminogen, chemically synthesized plasminogen, and recombinant plasminogen.

12. The process of claim 5 wherein said conversion is accomplished by urokinase or tissue plasminogen activator or active analogs thereof.

13. The process of claim 1 wherein a stabilized, fibrinolytically/fibrinogenolytically inhibited plasmin, or an analog thereof, is converted to fibrinolytically/fibrinogenolytically active plasmin, substantially coincident with said parenteral introduction, by exposing said stabilized plasmin to an inhibitor remover capable of removing the inhibitor of active plasmin, wherein said removal results in reactivation of said plasmin.

14. The process of claim 13 wherein said inhibitor comprises lauryl sulfate ions.

15. The process of claim 1 wherein said parenteral introduction of said active plasmin is continuous or intermittent for between two minutes and 28 days.

16. The process of claim 15, said introduction of said active plasmin being continuous or intermittent for between two minutes and 7 days.

17. A method of dissolving an intravascular thrombus in a human patient comprising administering parenterally to the patient a therapeutically effective amount of purified plasmin selected from the group consisting of miniplasmin, microplasmin, lys-plasmin, fibrinolytically active analogs thereof, and human plasmin, for a time and at a concentration sufficient to dissolve said thrombus, wherein, substantially coincident with said parenteral administration of said plasmin to said patient, fibrinolytically/fibrinogenolytically plasminogen, or an analog thereof, is converted to said plasmin ex vivo.

18. A method of reducing the risk of thrombus formation in a patient at risk for thrombus formation comprising administering parenterally to the patient a therapeutically effective amount of purified plasmin selected from the group consisting of miniplasmin, microplasmin, lys-plasmin, fibrinolytically active analogs thereof, and human plasmin, for a time and at a concentration sufficient to prevent the formation of a thrombus, wherein, substantially coincident with said parenteral administration of said plasmin to said patient, fibrinolytically/fibrinogenolytically plasminogen, or an analog thereof, is converted to said plasmin ex vivo.

* * * * *